United States Patent [19]
Gerbal

[11] 3,970,454
[45] July 20, 1976

[54] PHOTOGRAPHIC DEVELOPING AGENTS

[75] Inventor: Claude Fernand Marcel Gerbal, Bonneuil-sur-Marne, France

[73] Assignee: Eastman Kodak Company, Rochester, N.Y.

[22] Filed: Dec. 30, 1974

[21] Appl. No.: 537,221

[30] Foreign Application Priority Data
Jan. 10, 1974 France .............................. 74.00770

[52] U.S. Cl. .............................. 96/29 D; 96/66 HD; 96/66 R; 260/283 S; 260/286 Q; 260/288 R
[51] Int. Cl.² .................. G03C 5/30; C07D 215/00; C07D 215/58; C07D 215/12
[58] Field of Search ........ 260/283 R, 283 S, 288 R, 260/286 Q; 96/66 R, 29 D, 66.3, 66.4, 66.5, 66 HD

[56] References Cited
UNITED STATES PATENTS

| | | | |
|---|---|---|---|
| 2,163,820 | 6/1939 | Wilmanns et al. | 96/66 R |
| 2,196,739 | 4/1940 | Peterson | 96/66 R |
| 2,387,751 | 10/1945 | Dickey et al. | 96/66 HD |
| 2,566,132 | 8/1951 | Leffler | 260/286 Q |
| 2,566,259 | 8/1951 | Thirtle et al. | 96/66 HD |
| 2,886,436 | 5/1959 | Schmidt et al. | 96/55 |
| 3,262,906 | 7/1966 | Perry | 260/283 R |
| 3,615,525 | 10/1971 | Willems | 96/66 R |

FOREIGN PATENTS OR APPLICATIONS

| | | | |
|---|---|---|---|
| 1,110,521 | 7/1961 | Germany | 96/66 R |
| 371 | 11/1896 | United Kingdom | 96/66 R |

*Primary Examiner*—Mary F. Kelley
*Attorney, Agent, or Firm*—A. P. Lorenzo

[57] ABSTRACT

A new class of photographic developing agents of the p-aminophenol type are compounds of the formula:

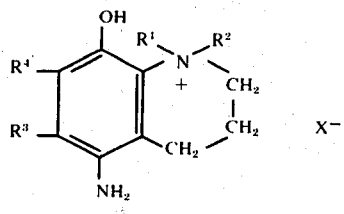

wherein
$R^1$ is an alkyl group of 1 to 12 carbon atoms;
$R^2$ is an alkyl group of 1 to 12 carbon atoms or a sulfoalkyl group of 1 to 12 carbon atoms,
$R^3$ is a hydrogen atom or an alkyl group of 1 to 12 carbon atoms,
$R^4$ is a hydrogen atom or an alkyl group of 1 to 12 carbon atoms, and $X^-$ is an anion with the proviso that when $R^2$ is a sulfoalkyl group then $X^-$ is the sulfo radical of $R^2$.

These compounds are useful as color developing agents, especially in diffusion transfer processes, and have been found to provide advantageous characteristics as compared with conventional developers of the p-amino-phenol type, for example, a substantial decrease in the formation of unwanted color stain in the receiving layer employed in diffusion transfer processes.

8 Claims, No Drawings

PHOTOGRAPHIC DEVELOPING AGENTS

This invention relates in general to photography and in particular to photographic color development. More specifically this invention relates to novel compounds of the p-aminophenol type which are color developing agents, to aqueous photographic developing solutions containing such compounds, and to a novel process for forming a photographic dye image by use of such compounds.

In the processes of color photography, one usually uses developers of the p-phenylenediamine type which, by reaction with coupling agents, form dye images. These processes are described in the literature, e.g., in the "*Encyclopedia of Chemical Technology*", Vol. 5, pages 812–845 (1964) by Thirtle. During color development, the silver halides, in the presence of the latent image, are reduced to metallic silver by the color developer, which is thus oxidized. The oxidation products of the color developer couple with the dye-forming compounds, such as coupling agents, so as to form a dye image corresponding to the silver image.

Use of developers of the p-aminophenol type in color photographic processes is also known. For example, U.S. Pat. No. 3,108,001 describes developers of the p-aminophenol series having the formula:

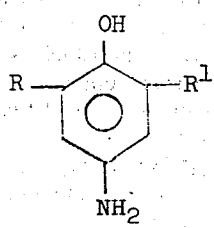

wherein R and $R^1$ are alkyl groups or alkoxy groups, and their use in diffusion transfer processes.

Developers derived from p-aminophenol have been less frequently used than those derived from p-phenylenediamines, at least in part as a result of their tendency to form dyes that are lacking in stability. Dye stability is only one factor in the selection of a photographic color developing agent however and novel compounds which are to be used as color developing agents must meet a variety of criteria. For example, color developing agents which are to be used in diffusion transfer processes need to be evaluated with respect to several factors, including: (1) the ability of the compound to develop a silver image as measured by the negative image silver coverage, (2) the ability of the compound to yield a dye image of adequate density as measured by the chromogenic yield, i.e., the ratio of the $D_{max}$ of the dye image to the negative image silver coverage, (3) the density of colored stain which is mordanted on the receiving layer, e.g. stain formed by oxidation products of the developing agent such as reaction products produced by reaction between reduced species and oxidized species of the developing agent which undergo a so-called "self-coupling" reaction, and (4) the shape of the spectral absorption curve of each dye image. Color developing agents of the p-aminophenol type which were known prior to the present invention have generally been deficient with respect to one or more of the four characteristics mentioned above. For example, a serious problem with prior art developing agents of the p-aminophenol type has been that the density of colored stain which is mordanted on the receiving layer is too high, particularly the yellow $D_{min}$ resulting from oxidation products of the developing agent. A further problem is that the shape of the spectral absorption curves of the dye images is often unsatisfactory, particularly in that the cyan dye images sometimes present spectral absorption curves which are markedly shifted toward infra-red radiation. While the silver image developing capability of p-aminophenol developing agents is generally quite good, some compounds of this type are less than satisfactory as regards chromogenic yield, as well as suffering from the disadvantages of stain formation and unwanted curve shifts.

It has now been discovered that certain novel compounds of the p-aminophenol series are useful as color developing agents, in both conventional processes of color photography and diffusion transfer processes, and that these compounds form stable dyes and exhibit a desirable combination of advantageous characteristics as developing agents. These compounds are represented by the formula:

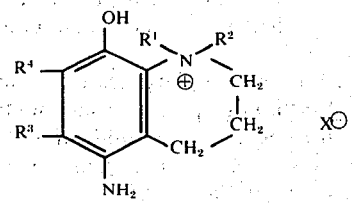

wherein
$R^1$ is an alkyl group of 1 to 12 carbon atoms, preferably of 1 to 4 carbon atoms,
$R^2$ is an alkyl group of 1 to 12 carbon atoms, preferably of 1 to 4 carbon atoms, or a sulfoalkyl group of 1 to 12 carbon atoms, preferably of 1 to 4 carbon atoms,
$R^3$ is a hydrogen atom or an alkyl group of 1 to 12 carbon atoms, preferably of 1 to 4 carbon atoms,
$R^4$ is a hydrogen atom or an alkyl group of 1 to 12 carbon atoms, preferably of 1 to 4 carbon atoms,
and $X^-$ is an anion such as chloride or bromide with the proviso that when $R^2$ is a sulfoalkyl group then $X^-$ is the sulfo radical of $R^2$.

Examples of preferred color developers within the scope of the above formula include the following compounds:

| Number | Color Developer |
|---|---|
| 1 | N,N-dimethyl-1,2,3,4-tetrahydro-5-amino-8-hydroxyquinolinium bromide |
| 2 | N,N-diethyl-1,2,3,4-tetrahydro-5-amino-8-hydroxyquinolinium bromide |
| 3 | N,N-dimethyl-1,2,3,4-tetrahydro-5-amino-7-propyl-8-hydroxyquinolinium bromide |
| 4 | N-methyl-N-(3-sulfobutyl)-1,2,3,4-tetrahydro-5-amino-8-hydroxyquinoline. |

The color developers described above are typically employed in aqueous alkaline color developing solutions. The concentration of color developer employed in such solution can be varied considerably, depending upon the solubility of the developer at the pH that is utilized.

Developer solutions prepared in accordance with this invention can contain a variety of agents in addition to the color developing agent. For example, they can contain alkali metal salts such as chlorides, bromides, iodides, sulfites, sulfates, carbonates, hydroxides, metaborates, phosphates, etc; buffering agents; ethylenediamine; citrazinic acid; inhibitors such as 5-nitro-benzimidazole; auxiliary developers such as 1-phenyl-3-pyrazolidones; stabilizers such as diethylhydroxylamine, dihydroxyacetone, glycolaldehyde, glyceraldehyde, dihydroxymaleic acid, etc; sequestering agents; etc.

The process according to the invention for forming a dye image in a photographic product consists in processing this product after exposure, in the presence of a coupling agent, with a developing agent according to the invention, so that the coupling agent couples with developing agent that has been oxidized by the latent image formed in the course of exposure, so as to obtain a dye image.

According to one embodiment of the invention, one forms an image of diffusible dye which one transfers to a receiving layer.

The dye-forming coupling agents, useful for carrying out of this embodiment of the invention, comprise any coupling agent whatsoever which is useful in diffusion-transfer processes.

These dye-forming coupling agents are initially non-diffusible in the photographic emulsion but form diffusible dyes in the course of development with the developers of the invention. Such coupling agents include those represented by the formula:

COL - LINK - (COUP - BALL)$_n$ and

BALL-LINK-(COUP SOL )$_n$ wherein
COL is a dye group containing an acid solubilizing radical,
LINK is a bond such as —N=N—, azoxy, mercury, oxy, alkylidene, thio, or dithio,
COUP is a photographic dye-forming coupling agent such as 5-pyrazolone, the coupling agent being substituted in the coupling position by the radical LINK,
BALL is a ballast group,
SOL is a solubilizing acid group, or a hydrogen atom, and
$n$ is a whole number equal to 1 or 2 when LINK represents an alkylidene radical, and equal to 1 when LINK represents, e.g. an azo, azoxy, mercury, oxy, thio, or dithio radical. Coupling agents of this type are described in U.S. Pat. No. 3,227,550.

One may use the developing agents of this invention in conventional processes of color development, as well as in diffusion-transfer processes.

The following examples illustrate the invention:

EXAMPLE 1

The compound N,N-dimethyl-1,2,3,4,-tetrahydro-5-amino-8-hydroxyquinolinium bromide (Compound No. 1), which has the formula:

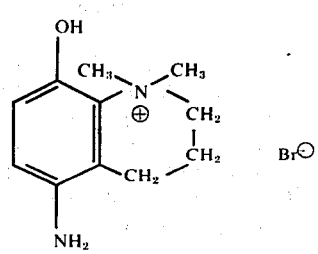

can be prepared as follows:

a. Preparation of N-methyl-8-hydroxyquinolinium methylsulfate

Into a 2-liter three-neck flask provided with a mechanical agitator, with a reflux-condenser and calcium chloride tube, and with a dropping funnel, one introduces 145 g of 8-hydroxyquinoline (i.e. 1 mole) and 200 ml of dimethyl acetamide. After dissolution of the 8-hydroxyquinoline, one cools the reaction mixture with a bath of ice water and one adds, drop by drop, by means of the dropping funnel, 126 g of freshly distilled methylsulfate (i.e. 1 mole). Shortly after the completion of the addition, a light yellow compound crystallizes little by little. One continues the agitation for 2 hours after the introduction of the methylsulfate and then leaves the mixture to rest overnight in a brine bath. The quaternary salt which is formed is dried, washed with anhydrous ether and recrystallized in methanol. Weight obtained = 219 g; Melting point = 158°C; Yield = 81%.

Analysis: $C_{11}H_{13}NO_5S$ (271): Calculated % : C, 48.70; H, 4.79; N, 5.16; S, 11.80. Found : C, 48.50; H, 4.75; N, 5.13; S, 12.12 b. Preparation of N-methyl-8-hydroxy-1,2,3,4-tetrahydroquinoline

One introduces into a steel autoclave 54.2 g of N-methyl-8-hydroxyquinolinium methylsulfate (i.e. 0.2 mole) in 100 ml of water and 5 g of activated Raney nickel. The hydrogenation is effected under a hydrogen pressure of from 70 to 80 kg/cm$^2$, at a temperature of 80°C. After cooling, one filters off the catalyst and one neutralizes with an ammonia solution. One dries the crystallized product that is formed and one recrystallizes it in methanol.

Weight obtained = 25 g; Melting Point = 110°C; Yield = 76.5%.

Analysis: $C_{10}H_{13}NO$(163): Calculated % : C, 73.61; H, 7.97; N, 8.58. Found : C, 73.75; H, 8.17; N, 8.69.

c. Preparation of N,N-dimethyl-1,2,3,4-tetrahydro-8-hydroxyquinolinium bromide Into a stainless steel autoclave, one introduces 163 g of N-methyl-8-hydroxy-1,2,3,4-tetrahydroquinoline (i.e. 1 mole), 400 ml of acetonitrile and 100 ml of methyl bromide. One heats in an oil bath, at 60°C, for 90 hours. After cooling, one dries the brown compound that is formed. One evaporates the solvent, and combines the evaporation residue with the preceding fraction. The weight of crude quaternary salt that is obtained is equal to 220 g. One recrystallizes in 500 ml of ethanol, filters, and dries.

Weight obtained = 152 g.; Melting point = 255°C; Yield = 60%.

Analysis: C₁₁H₁₆NOBr(258): Calculated: C, 51.16; H, 6.20; N, 5.42; Br, 31.00. Found C, 50.78; H, 6.13; N, 5.47; Br, 30.93.

It is to be noted that the boiling point of methyl bromide being very low (the boiling point under a pressure of 760 mm of Hg is equal to 4.5°C), it is necessary to thoroughly cool the autoclave and dropping funnel with a mixture of acetone and solid carbon dioxide before handling.

d. Preparation of N,N-dimethyl-1,2,3,4-tetrahydro-5-phenylazo-8-hydroxyquinolinium bromide 1. Preparation of benzene diazonium bromide Into a 4-liter three-neck flask, provided with a thermometer, a mechanical agitator, and a dropping funnel, one introduces 93 g of aniline (i.e. 1 mole), 500 ml of water and 425 g of 48% hydrobromic acid (i.e. 2.5 moles). To this mixture, maintained between 0°C and 4°C, one adds a solution of 70 g of sodium nitrite in 100 ml of water.

2. Coupling reaction

Into a 4-liter three-neck flask, provided with a thermometer, a mechanical agitator, and a dropping funnel, one introduces 500 ml of water, 40 g of sodium hydroxide (1 mole), 53 g of sodium carbonate (0.5 mole) and 258 g of N,N-dimethyl-1,2,3,4-tetrahydro-8-hydroxyquinolinium bromide (i.e. 1 mole). To this solution one adds, drop by drop, by means of a dropping funnel, the cooled solution (0° to 5°C) of the benzene diazonium bromide, while agitating energetically. The temperature must be maintained between 5°C and 8°C during coupling. An orange colored dye is formed. One continues the agitation for 2 hours after completion of the addition of the diazonium salt. One filters the dye and recrystallizes it in 11 liters of ethanol. Weight obtained = 256 g; Melting point = 245°C; Yield = 73%.

Analysis: C₁₇H₂₀N₃OBr(362): Calculated: C, 56.35; H, 5.52; N, 11.60; Br, 22.09. Found: C, 55.85; H, 5.62; N, 11.43; Br, 22.06.

e. Preparation of N,N-dimethyl-1,2,3,4-tetrahydro-5-amino-8-hydroxyquinolinium bromide Into a stainless steel autoclave, one introduces 36.2 g of N,N-dimethyl-1,2,3,4-tetrahydro-5-phenylazo-8-hydroxyquinolinium bromide (i.e. 0.1 mole), 200 ml of methanol and 3 g of 5% palladium on charcoal. The reduction is carried out at a pressure of 3–5 kg/cm² of hydrogen and a temperature of 50°–60°C. After cooling, one adds a sufficient quantity of water to dissolve the entire mass, then one filters off the catalyst. One evaporates the filtrate to the dry state. The residue is extracted by means of ether so as to remove the aniline. One washes, with acetone, the clear brown compound that is obtained.

Weight obtained = 2.5 g.; Melting point = 258°C; Yield = 95%.

Analysis: C₁₁H₁₇N₂OBr(269): Calculated % : C, 49.07; H, 6.31; N, 10.4; Br, 29.74. Found: C, 48.07; H, 6.30; N, 10.23; Br, 29.15.

EXAMPLE 2

The compound N,N-diethyl-1,2,3,4-tetrahydro-5-amino-8-hydroxyquinolinium bromide (Compound No. 2) which has the formula:

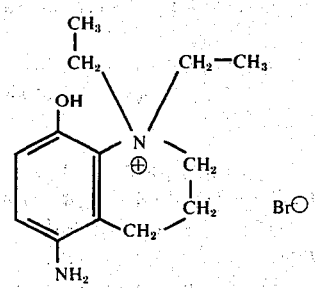

can be prepared as follows:

a. Preparation of N-ethyl-8-hydroxyquinolinium ethylsulfate

Into a 2-liter three-neck flask, provided with a mechanical agitator, with a reflux condenser and calcium chloride tube, and with a dropping funnel, one introduces 580 g of 8-hydroxyquinoline (i.e. 4 moles) and 800 ml of dimethylacetamide. After dissolution of the 8-hydroxyquinoline one adds, drop by drop, 616 g of freshly distilled ethyl sulfate, and then cools the reaction mixture with a bath of ice water. After heating on a steam bath for 2 hours, the solution becomes orange-yellow. One removes the dimethylformamide by means of distillation in a water-jet pump vacuum. The yellow residue is washed with anhydrous ether. The quaternary salt crystallizes after scraping. One recrystallizes the quaternary salt by dissolution in isopropanol at the rate of 1 g of quaternary salt per 1.5 ml of isopropanol. One obtains 920 g of yellow crystals which are washed thoroughly with ethyl ether.

Melting point = 95°C; Yield = 78.6%.

Analysis: C₁₃H₁₇NO₅S (299) Calculated %: C, 52.17; H, 5.68; N, 4.68; S, 10.70. Found: C, 52.08; H, 5.61; N, 4.72; S, 10.44.

b. Preparation of N-ethyl-1,2,3,4-tetrahydro-8-hdyroxyquinoline

Into a stainless steel autoclave, one introduces 150 g of 8-hydroxyquinolinium ethylsulfate (i.e. 0.5 mole) in 250 ml of water and 5 g of activated Raney nickel. The hydrogenation is carried out under 70 to 80 kg/cm² hydrogen pressure, at a temperature of 80°C. After cooling, one filters off the catalyst, and neutralizes with an ammonia solution. One dries the crystalline compound that is formed and recrystallizes it in isopropanol (1 g of product per 2 ml of alcohol). One obtains 78 g of light beige crystals, i.e. a yield of 88%.

Melting point = 52°C.

Anal.: C₁₁H₁₅NO (177): Calc. %: C, 74.56; H, 8.46; N, 7.91. Found: C, 74.27; H, 8.42; N, 7.75.

c. Preparation of N,N-diethyl-1,2,3,4-tetrahydro-8-hydroxyquinoline bromide

Into a stainless steel autoclave, one introduces 36 g of N-ethyl-1,2,3,4-tetrahydro-8-hydroxyquinoline (i.e. 0.2 mole), 22 g of ethyl bromide (i.e. 0.2 mole) and 25 ml of acetonitrile. One heats in an oil bath at 120°–130°C. After cooling, one removes the solvent by means of distillation. The gray-white quaternary salt that is obtained is washed with anhydrous ether, then recrystallized in ethanol, at a ratio of 1 g of product per 3 ml of alcohol. The pinkish-white crystals that are obtained are filtered, then washed again with anhydrous ether.

Weight obtained: 45 g. Melting point = 208°C; Yield = 79%.

Anal.: C₁₃H₂₀NOBr (286): Calc. %: C, 54.54; H, 6.99; N, 4.89; Br, 27.96. Found: C, 53.85; H, 7.07; N, 4.70; Br, 27.99.

d. Preparation of N,N-diethyl-1,2,3,4-tetrahydro-5-phenylazo-8-hydroxyquinolinium bromide 1. Preparation of benzene diazonium bromide Into a 1-liter three-neck flask, provided with a mechanical agitator and with a thermometer, one introduces 38 g of aniline (i.e. 0.4 mole), 200 ml of water and 170 g of hydrobromic acid (48% solution). One maintains the temperature at 0°C, by means of an ice bath, and one adds, drop by drop, a solution of sodium nitrite (28 g of nitrite in 40 ml of water). One agitates for 20 minutes after the completion of the addition of the nitrite. The light yellow solution that one obtains is kept in ice.

2. Coupling

Into a 2-liter three-neck flask, one introduces 16 g of sodium hydroxide (0.4 mole), in 200 ml of water, and then adds 21.2 g of sodium carbonate (i.e. 0.2 moles). When the solution is clear, one adds little by little 116 g of 1,2,3,4-tetrahydro-8-hydroxyquinolinium bromide. The solution becomes light brown. At 0°C, one adds the above-prepared solution of benzene diazonium bromide in small portions. A rubbery brown-red dye is formed.

3. Purification

One dissolves the dye in a minimum amount of ethanol, evaporates the solvent, adds anhydrous ether, decants and dries.

Weight obtained = 130 g. Melting point = 230°C. Yield = 83%.

Anal.: C₁₉H₂₄N₃OBr: (390).

e. Preparation of N,N-diethyl-1,2,3,4-tetrahydro-5-amino-8-hydroxyquinolinium bromide Into a stainless steel autoclave, one introduces 20 g of azo dye and 200 ml of water, one adds 3 g of 5% palladium on charcoal. Reduction is then carried out under a 10-kg hydrogen pressure and at a temperature of 70°-80°C. After the reduction is complete, one cools and filters out the catalyst. The aqueous solution is evaporated to dryness and a light gray compound is collected.

Weight obtained = 15 g.; Melting point = 178°C, (Quantitative yield).

Analysis: C₁₃H₂₁N₂OBr (301).

EXAMPLE 3

The compound N,N-dimethyl-1,2,3,4-tetrahydro-5-amino-7-propyl-8-hydroxyquinolinium bromide (Compound No. 3) which has the formula

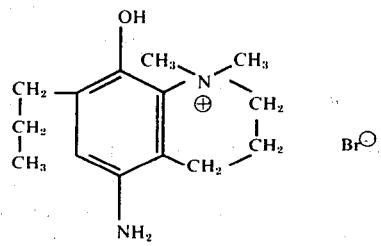

can be prepared as follows:

1. Allyloxy-8-quinoline

Into a three-neck flask, provided with a reflux condenser equipped with a CaCl₂ tube, one introduces 1,200 ml of methanol and one adds, little by little, while agitating mechanically, 46 g of sodium in small pieces. One adds 290 g of 8-hydroxyquinoline (i.e. 2 moles). When the mixture is homogeneous, one adds drop by drop, by means of a dropping funnel, 250 g of allyl bromide. One heats the reaction mixture on a steam bath. The solution, yellow at the beginning, becomes orange-yellow and then purplish-red. One heats for 6 hours under nitrogen atmosphere One removes the methanol by means of distillation, then one redissolves the residue in 2N sodium hydroxide solution. A red precipitate is formed that one filters, then one extracts the solution and the precipitate with ether. The ether extracts are dried over anhydrous sodium sulfate, then one filters the Na₂SO₄, and one removes the solvent by means of distillation. One fractionates the residue with a high vacuum pump. The allyloxy-8 quinoline distills at 114°C under a 0.25 mm Hg pressure. One obtains 237 g of a light yellow liquid. Yield = 88%.

Anal.: C₁₂H₁₁NO (185): Calc. %: C, 77.83; H, 5.94; N, 7.56. Found: C, 77.78; H, 6.11; N, 7.29.

2. 7-allyl-8-hydroxyquinoline

Claisen Reaction.

Into a 1-liter three-neck flask, provided with a mechanical agitator, one introduces 230 g of allyloxy-8-quinoline (i.e. 1.24 mole) in 650 ml of dimethyl aniline. The reaction mixture is swept with a stream of nitrogen and heated under reflux for 8 hours. The reaction mixture becomes reddish brown as the reaction proceeds. When the reaction is completed, one removes the dimethyl acetamide by a distillation (at 70°-72°C) under the vacuum formed by a water pump. The residue is then distilled under high vacuum. One collcts 208 g of a colorless liquid that distills at 98°C at 0.2 mm Hg pressure. The liquid crystallizes to a white solid. Yield = 90.5%.

Anal.: C₁₂H₁₁NO (185): Calc. %: C, 77.83; H, 5.94; N, 7.56. Found: C, 77.31; H, 5.97; N, 7.45.

3. Preparation of 7-propyl-8-hydroxyquinoline

Into a stainless steel autoclave, one introduces 93 g of 7-allyl-8-hydroxyquinoline (i.e. 0.5 mole), 250 ml of methanol, and 3 g of 5% palladium on charcoal. The hydrogenation is carried out under a 4 kg/cm² hydrogen pressure. After absorption of a sufficient quantity of hydrogen and cooling, one filters off the catalyst, removes the solvent by distillation under normal pressure, and then distills the residue under high vacuum. The 7-propyl-8-hydroxyquinoline distills at 105°-106°C at a pressure of 0.25 mm Hg. One collects 78 g of a light yellow liquid. Yield = 84.5%.

Anal: $C_{12}H_{13}NO(187)$: Calc. %: C, 77.00; H, 6.96; N, 7.49; O, 8.55. Found: C, 77.16; H, 7.01; N, 7.34; O, 8.49.

4. Preparation of N-methyl-7-propyl-8-hydroxyquinolinium paratoluenesulfonate

Into a 100 ml flask, one introduces 29 g of 7-propyl-8-hydroxyquinoline (i.e. 0.15 mole) and 29 g of methylparatoluene sulfonate (i.e. 0.15 mole) and then equips the flask with an upright reflux condenser and a calcium chloride tube. One heats at 80°C. for 24 hours. After cooling, one recovers with anhydrous ether the quaternary salt that is formed, one washes it two or three times and decants the ether after each washing. The quaternary salt crystallizes in the form of yellow crystals. One recrystallizes in boiling isopropanol. One washes the quaternary salt with ether and collects 43 g of lemon-yellow crystals, i.e. a yield of 75%.
Melting point = 128°C.

Anal.: $C_{20}H_{23}NO_4S$ (373): Calc. %: C, 64.34; H, 6.17; N, 3.76; S, 8.57. Found: C, 63.88; H, 6.14; N, 3.58; S, 8.79.

5. Preparation of N-methyl-1,2,3,4-tetrahydro-7-propyl-8-hydroxyquinoline

Into a stainless steel autoclave, one introduces 37.3 g of paratoluenesulfonate of N-methyl-7-propyl-8-hydroxyquinoline (0.1 mole) in 120 ml of water, and 5 g of Raney nickel. The hydrogenation is carried out under an 80 kg/cm² hydrogen pressure. After absorption of the hydrogen, one cools and filters off the catalyst; one neutralizes the filtrate with an ammonia solution, resulting in the formation of a grayish-white precipitate that one separates and distills under high vacuum. One collects 8 g of a colorless liquid that distills at 180°–110°C under a 0.5 mm Hg pressure. One obtains a yield of 36%.

Anal.: $C_{13}H_{19}HO$ (205): Calc. %: C, 76.05; H, 9.27; N, 6.83; O, 7.85. Found: C, 76.05; H, 9.51; N, 6.72; O, 7.72.

6. Preparation of N,N-dimethyl-1,2,3,4-tetrahydro-7-propyl-8-hydroxyquinolinium bromide Into a tube, one introduces 7.5 g of N-methyl-1,2,3,4-tetrahydro-7-propyl-8-hydroxyquinoline (i.e. 0.035 mole) and 4 g of methyl bromide (i.e. 0.035 mole). One adds 10 ml of acetonitrile, one seals the tube and one heats in an oil bath, at 70°C, for 90 hours. After cooling, one dries the compound that is formed, washes with anhydrous ether, and recrystallizes in boiling isopropanol (1 g of product, 2 ml of alcohol). One collects whitish crystals, which one washes again with ether, then one dries the resulting quaternary salt in a drier over sulfuric acid. One obtains 8 g of product, i.e. a yield of 735/1000.

Anal.: $C_{14}H_{22}NOBr$ (300): Calc. %: C, 56.00; H, 7.33; N, 4.66; Br, 6.66. Found: C, 55.95; H, 7.43; N, 4.62; Br, 26.79.

7. Preparation of N,N-dimethyl-1,2,3,4-tetrahydro-5-phenylazo-7-propyl-8-hydroxyquinolinium bromide a. Benzene diazonium bromide Into a three-neck flask, provided with a mechanical agitator, one introducess 9.3 g of aniline, 15 liters of water, and 50 g of 40% hydrobromic acid. One maintains the temperature between 0°C and 5°C, and one adds, drop by drop, a solution of 7 g of sodium nitrite in 10 ml of water, then one agitates vigorously.

b. Into a 500-ml three-neck flask, one introduces a sodium hydroxide solution (4 g in 50 ml of water) and 5 g of sodium carbonate, then one adds 30 g of the quaternary salt of 1,2,3,4-tetrahydroquinolinium bromide (0.1 mole). To this cooled solution, one adds slowly the previously prepared benzene diazonium bromide solution. The formation of a red dye occurs immediately. One continues the vigorous agitation for 1 hour in a brine bath. One filters the dye that is formed, recrystallizes it in acetonitrile, washes it with ether and dries it.
Weight obtained = 27 g.; Yield = 77% Melting point = 256°C.

Anal.: $C_{20}H_{26}N_3OBr(404)$: Calc. %: C, 59.4; H, 6.43; N, 10.39; Br, 19.80. Found: C, 60.4; H, 6.89; N, 10.73; Br, 19.40.

8. N,N-dimethyl-1,2,3,4-tetrahydro-5-amino-7-propyl-8-hydroxyquinolinium bromide One introduces into a stainless steel autoclave 15.75 g of N,N-dimethyl-1,2,3,4-tetrahydro-5-phenylazo-7-propyl-8-hydroxyquinolinium bromide (i.e. 0.05 mole) with 170 ml of water and 17 ml of methanol, and one adds 3 g of 5% palladium on charcoal. One hydrogenates under a 3 kg/cm² to 5 kg/cm² hydrogen pressure. After cooling, one filters off the catalyst, evaporates the filtrate, and redissolves the residue in ether so as to remove the aniline. One recrystallizes in acetonitrile and one washes again with ether.
Quantity obtained: 5g.

EXAMPLE 4

The compound N-methyl-N-(3-sulfobutyl)-1,2,3,4-tetrahydro-5-amino-8-hydroxyquinoline (Compound No. 4) which has the formula

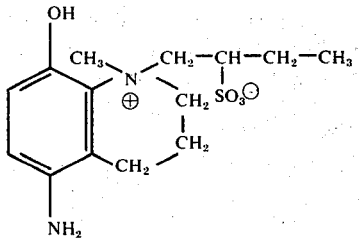

can be prepared as follows:

1. Preparation of N-methyl-N-(3-sulfobutyl)-1,2,3,4-tetrahydro-8-hydroxyquinoline Into a 100-ml flask, equipped with a reflux condenser and with a calcium chloride tube, one introduces 16.3 g of N-methyl-1,2,3,4-tetrahydro-8-hydroxyquinoline (i.e. 0.1 mole) and 13.6 g of 2,4-butane sulfone (i.e. 0.1 mole). One heats for 3 hours at the reflux temperature of methanol. After cooling, one pours the solution into pure dry ether. The quaternary salt is crystallized by means of scraping and filtered.
Obtained: 27 g of product, i.e. a yield of 93%.

Anal.: $C_{14}H_{21}NO_4S(M=299)$: Calc. %: C, 56.18; H, 7.02; N, 4.68; S, 10.70. Found: C, 55.79; H, 6.69; N, 4.71; S., 10.71.

2. Preparation of N-methyl N-(3-sulfobutyl)-1,2,3,4-tetrahydro-5-phenylazo-8-hydroxyquinoline a. Diazoaniline One diazotizes 9.3 g of aniline (i.e. 0.1 mole) in 25 ml of pure HCl and 30 ml of water, then one adds a solution of 7.1 g of sodium nitrite in 50 ml of water, while maintaining the temperature at 0°C.

b. Into a 250-ml three-neck flask, one introduces 27 g of N-methyl-N-(3-sulfobutyl-1,2,3,4-tetrahydro-8-hydroxyquinoline (i.e. 0.1 mole) in 100 ml of water and 4 g of sodium hydroxide. One slowly adds the diazoaniline while agitating mechanically and maintaining the temperature at 0°C. The formation of a red dye occurs. One continues the agitation for 2 hours after completion of the addition of the diazoaniline. One recrystallizes in a minimum of methanol and precipitates with pure ether. One filters off brown-red crystals. One obtains 20 g or product, i.e. a yield of 56%.

Anal.: $C_{20}H_{25}N_3O_4S(M=403)$: Calc. %: C, 59.55; H, 6.20; N, 10.42; S, 7.94. Found: C, 58.35; H, 5.77; N, 9.86; S, 7.53.

3. Preparation of N-methyl-N-(3-sulfobutyl)-1,2,3,4-tetrahydro-5-amino-8-hydroxyquinoline Into a 500-ml hydrogenation flask, one introduces 9.5 g of N-methyl-N-(3-sulfobutyl)-1,2,3,4-tetrahydro-5-phenylazo-8-hydroxyquinoline in 200 ml of methanol and 2 g of platinum oxide. One reduces under normal hydrogen pressure for 3 hours. After reduction, one filters off the catalyst, and removes the solvent by distillation under vacuum while applying a nitrogen stream through a capillary tube. One washes the residue with ether to remove the aniline. One recrystallizes by redissolving in methanol, precipitates with ether, filters, and dries under vacuum over $H_2SO_4$. One obtains 5 g of product, i.e. a yield of 72%.

Anal: $C_{14}H_{22}N_2O_4S(M=314)$: Calc. %: C, 52.60; H, 7.00; N, 8.91; S, 10.19. Found: C, 53.25; H, 6.47; N, 8.41; S, 9.83.

The following examples illustrate the use of the developing agents of this invention in a diffusion transfer process.

EXAMPLE 5

A. One prepares three negative photosensitive products comprising a photosensitive silver halide emulsion layer containing 10 mg/dm² of silver, 25 mg/dm² of gelatin, and 10 mg/dm² of coupling agent. The three photosensitive products are identical except for the coupling agent, which is 1-hydroxy-4[alpha(3'-pentadecyl-phenoxy)butylamido]-phenoxy-N-ethyl (2'',-5''-dicarboxy)-2-naphthanilide, (cyan), 1 phenyl-3-(3,5-dicarboxyanilino)-4-(m-octadecylcarbamyl phenylthio)-5-pyrazolone (magenta), and alpha-pivalylalpha(3-pentadecyl-4-nitro phenoxy)-4-sulfamylacetanilide, (yellow), respectively.

One exposes the photographic product in a variable-density sensitometer, then one processes it in contact with a transparent image-receiving sheet, consisting of a mordant layer containing the chloride of copoly[styrene-(N,N-dimethyl-N-benzyl-N-3-maleimidopropyl-)ammonium] applied to a triacetate support, (for periods of 1 minute and 30 seconds, respectively, at a temperature of 23°C) by means of a viscous processing composition containing the following components:

N-N-dimethyl-1,2,3,4-tetrahydro-5-amino-8-hydroxy-
quinolinium bromide (Compound No. 1)     0.05M
—NaOH     0.5 M
-hydroxyethylcellulose (thickening agent)     10 g/l
-anti-oxidant(piperidino-hexose-reductone)     0.8 g/l One then separates the receiving sheet that carries a dye image, of good quality, negative with respect to the original. One washes the receiving sheet for 1 minute and then dries it. One then measures the maximum density of the image that was obtained. One also determines by means of X-ray fluorescence the amount of silver developed after 30 seconds and 1 minute, respectively, in the original films that have been fixed after development by a conventional fixing agent, i.e. one determines the negative image silver coverage in milligrams of silver per square decimeter (mg Ag°/dm²). The results that are obtained are given in Table I.

B. One repeats the procedure described above but uses a processing composition that contains p-aminophenol as the developing agent and one measures the maximum density of the dye image, as well as the amount of silver developed after 30 seconds and 1 minute, respectively.

EXAMPLE 6

One repeats the process described in Example 5, except that the color developer that is used in the processing composition is N,N-diethyl-1,2,3,4-tetrahydro-5-amino-8-hydroxyquinolinium bromide (Compound No. 2). The results obtained are given in Table I.

EXAMPLE 7

One repeats the process described in Example 5, except that the color developer that is used in the processing composition is N,N-dimethyl-1,2,3,4-tetrahydro-5-amino-7-propyl-8-hydroxyquinolinium bromide (Compound No. 3).

The results obtained are given in Table I.

EXAMPLE 8

One repeats the process described in Example 5, except that the color developer that is used in the processing composition is N-methyl-N-(3-sulfobutyl)-1,2,3,4-tetrahydro-5-amino-8-hydroxyquinoline (Compound No. 4).

The results obtained are given in Table 1.

TABLE I

| Color Developer | Developed Silver (mg Ag°/dm²) 30 seconds | 1 minute | Fog (mg Ag°/dm²) | Chromogenic Yield ($D_{max}/Ag°$) with yellow coupling agent | with magenta coupling agent | with cyan coupling agent |
|---|---|---|---|---|---|---|
| p-aminophenol | 5.9 | 7.1 | 0.70 | 0.28 | 0.29 | 0.27 |
| Compound No. 1 | 4.87 | 6.33 | 0.13 | 0.14 | 0.42 | 0.42 |
| Compound No. 2 | 4.43 | 5.08 | 0.26 | 0.15 | 0.32 | 0.49 |
| Compound No. 3 | 3.97 | 4.53 | 0.64 | 0.47 | 0.35 | 0.56 |
| Compound No. 4 | 5.30 | 6.40 | 0.90 | 0.20 | 0.16 | 0.25 |

The data reported in Table I show that the color developing agents of this invention provide good results with respect to both negative image silver coverage and chromogenic yield.

EXAMPLE 9

One prepares a negative photographic product, comprising a photosensitive silver halide emulsion layer containing 10 mg/dm² of silver, 25 mg/dm² of gelatin and no coupling agent, applied to a cellulose triacetate support. One exposes the photographic product in a variable-density sensitometer, then one processes it in contact with a transparent image-receiving sheet that contains a mordant, as described in Example 5, for 1 minute, at a temperature of 23°C, with a viscous processing composition comprising:

—NaOH  0.5 M
-Hydroxyethylcellulose (thickening agent)  10 g/l
-Piperidino-hexose-reductone  0.8 g/l and a color developing agent selected from the group consisting of:

para-aminophenol
N,N-dimethyl-1,2,3,4-tetrahydro-5-amino-8-hydroxyquinolinium bromide (Compound No. 1)
N,N-diethyl-1,2,3,4-tetrahydro-5-amino-8-hydroxyquinolinium bromide (Compound No. 2)
N,N-dimethyl-1,2,3,4-tetrahydro-5-amino-7-propyl-8-hydroxyquinolinium bromide (Compound No. 3)
N-methyl-N-(3-sulfobutyl)-1,2,3,4-tetrahydro-5-amino-8-hydroxyquinoline (Compound No. 4)

in a quantity of 0.05 M.

One then separates the receiving sheet, washes it and dries it and then one measures the density of colored stain. When the silver negative has been fixed after development, by means of a conventional fixing agent, one measures the developed silver mass. One may then calculate the ratio of colored stain density to the quantity of developed silver, so as to make comparisons between p-aminophenol and the developing agents of the invention.

The results obtained are given in Table II. These results show that the amount of colored stain obtained with the developing agents of this invention is below the quantity obtained with p-aminophenol, (one obtains, for example, a ratio of 0.06 with p-aminophenol and of 0.015 with Compound No. 1).

The examples given above illustrate the effectiveness of the compounds of this invention as color developing agents in diffusion transfer processes. Thus, the compounds of this invention are advantageous in that they provide good negative image silver coverage, good chromogenic yield, and very little colored stain. This reduction in colored stain is particularly significant and is believed to be attributable, at least in part, to the fact that these developing agents form oxidation products that have a low propensity to be mordanted on the dye-image receiving layer. The color developing agents of this invention are also advantageous in that they provide dyes with good stability and provide desirable spectral absorption curves in each dye image, for example, absorption curves of the cyan dye images that are within the visible portion of the spectrum rather than being shifted toward the infra-red.

tions can be effected within the spirit and scope of the invention.

What is claimed is:

1. A compound of the formula:

wherein
R$^1$ is an alkyl group of 1 to 12 carbon atoms,
R$^2$ is an alkyl group of 1 to 12 carbon atoms or a sulfoalkyl group of 1 to 12 carbon atoms,
R$^3$ is a hydrogen atom or an alkyl group of 1 to 12 carbon atoms,
R$^4$ is a hydrogen atom or an alkyl group of 1 to 12 carbon atoms, and X$^-$ is an anion with the proviso that when R$^2$ is a sulfoalkyl group then X$^-$ is the sulfo radical of R$^2$.

2. The compound N,N-dimethyl-1,2,3,4-tetrahydro-5-amino-8-hydroxyquinolinium bromide.

3. The compound N,N-diethyl-1,2,3,4-tetrahydro-5-amino-8-hydroxyquinolinium bromide.

4. The compound N,N-dimethyl-1,2,3,4-tetrahydro-5-amino-7-propyl-8-hydroxyquinolinium bromide.

5. The compound N-methyl-N-(3-sulfobutyl)-1,2,3,4-tetrahydro-5-amino-8-hydroxyquinoline.

6. An aqueous alkaline photographic color developing solution containing a developing agent of the formula:

wherein
R$^1$ is an alkyl group of 1 to 12 carbon atoms,
R$^2$ is an alkyl group of 1 to 12 carbon atoms or a

TABLE II

| Color Developer | Density of Colored Stain | Ratio of Colored Stain Density to Quantity of Developed Silver |
|---|---|---|
| p-aminophenol | 0.47 for a development of 7.75 mg of Ag° | 0.06 |
| Compound No. 1 | 0.08 for a development of 5.5 mg of Ag° | 0.015 |
| Compound No. 2 | 0.02 for a development of 4.59 mg of Ag° | 0.045 |
| Compound No. 3 | 0.03 for a development of 4.3 mg of Ag° | 0.007 |
| Compound No. 4 | 0.20 for a development of 6.5 mg of Ag° | 0.03 |

The invention has been described in detail with particular reference to preferred embodiments thereof, but it will be understood that variations and modificasulfoalkyl group of 1 to 12 carbon atoms,
R$^3$ is a hydrogen atom or a alkyl group of 1 to 12 carbon atoms, R⁴ is a hydrogen atom or an alkyl group of 1 to 12 carbon atoms, and X⁻ is an anion with the proviso that where R² is a sulfoalkyl group then X⁻ is the sulfo radical of R².

7. An aqueous alkaline photographic color developing solution containing a developing agent selected from the group consisting of
N,N-dimethyl-1,2,3,4-tetrahydro-5-amino-8-hydroxyquinolinium bromide,
N,N-diethyl-1,2,3,4-tetrahydro-5-amino-8-hydroxyquinolinium bromide,
N,N-dimethyl-1,2,3,4-tetrahydro-5-amino-7-propyl-8-hydroxyquinolinium bromide, and
N-methyl-N-(3-sulfobutyl)-1,2,3,4-tetrahydro-5-amino-8-hydroxyquinoline.

8. In a process of forming a photographic dye image by diffusion transfer in which an imagewise exposed photographic element, comprising at least one silver halide emulsion layer with which is associated a dye-forming coupling agent, is treated with a basic composition in the presence of a color developing agent to obtain an imagewise distribution of a diffusible dye which is permitted to diffuse to a dye-receiving layer, the improvement wherein said color developing agent is a compound of the formula:

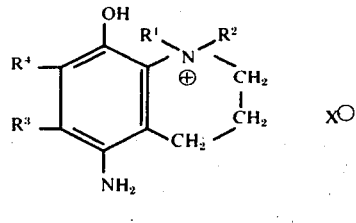

wherein
R¹ is an alkyl group of 1 to 12 carbon atoms,
R² is an alkyl group of 1 to 12 carbon atoms, or a sulfoalkyl group of 1 to 12 carbon atoms,
R³ is a hydrogen atom or an alkyl group of 1 to 12 carbon atoms,
R⁴ is a hydrogen atom or an alkyl group of 1 to 12 carbon atoms, and X⁻ is an anion with the proviso that when R² is a sulfoalkyl group then X⁻ is the sulfo radical of R².

* * * * *